(12) United States Patent
Saygili

(10) Patent No.: US 10,820,620 B2
(45) Date of Patent: Nov. 3, 2020

(54) CARTRIDGE ASSEMBLY HAVING A SLIDING CARTRIDGE BODY

(71) Applicant: Philip Morris Products S.A., Neuchatel (CH)

(72) Inventor: Ali Murat Saygili, Neuchatel (CH)

(73) Assignee: Philip Morris Products S.A., Neuchatel (CH)

( * ) Notice: Subject to any disclaimer, the term of this patent is extended or adjusted under 35 U.S.C. 154(b) by 257 days.

(21) Appl. No.: 16/069,569

(22) PCT Filed: Jan. 25, 2017

(86) PCT No.: PCT/EP2017/051542
§ 371 (c)(1),
(2) Date: Jul. 12, 2018

(87) PCT Pub. No.: WO2017/129613
PCT Pub. Date: Aug. 3, 2017

(65) Prior Publication Data
US 2019/0045833 A1    Feb. 14, 2019

(30) Foreign Application Priority Data

Jan. 25, 2016  (EP) .................................. 16152631

(51) Int. Cl.
*A24F 47/00*        (2020.01)
*A24B 15/167*       (2020.01)
(Continued)

(52) U.S. Cl.
CPC .......... *A24B 15/167* (2016.11); *A24F 47/008* (2013.01); *A61M 11/042* (2014.02);
(Continued)

(58) Field of Classification Search
CPC ...................................................... A24F 40/40
See application file for complete search history.

(56) References Cited

U.S. PATENT DOCUMENTS

| 4,989,619 A | 2/1991 | Clearman et al. |
| 2014/0034070 A1 | 2/2014 | Schennum |

(Continued)

FOREIGN PATENT DOCUMENTS

| AU | 2012347292 A1 | 7/2014 |
| CN | 1102964 A | 5/1995 |

(Continued)

OTHER PUBLICATIONS

International Search Report and Written Opinion dated Mar. 6, 2017 in PCT/EP2017/051542 filed Jan. 25, 2017.

(Continued)

*Primary Examiner* — Eric Yaary
(74) *Attorney, Agent, or Firm* — Oblon, McClelland, Maier & Neustadt, L.L.P.

(57) ABSTRACT

A cartridge assembly for an aerosol-generating system is provided, including a cartridge and a mouthpiece. The cartridge includes a cartridge body including a first compartment and a second compartment each having an air inlet and an air outlet. The cartridge further includes an enclosure comprising air inlets and air outlets, wherein the cartridge body is slidably received within the enclosure. The mouthpiece includes a mouthpiece cavity configured to receive the cartridge. The cartridge body is configured to slide with respect to the enclosure from a first position to a second position when the cartridge is inserted into the mouthpiece cavity. In the first position, the enclosure obstructs the air inlets and air outlets of the cartridge body. In the second position, the air inlets and the air outlets of the enclosure are in fluid communication with the corresponding air inlets and air outlets of the cartridge body.

17 Claims, 3 Drawing Sheets

(51) Int. Cl.
*A61M 15/06* (2006.01)
*A61M 11/04* (2006.01)

(52) U.S. Cl.
CPC ..... *A61M 15/06* (2013.01); *A61M 2205/3368* (2013.01); *A61M 2205/3653* (2013.01)

(56) References Cited

U.S. PATENT DOCUMENTS

| | | |
|---|---|---|
| 2014/0182608 A1 | 7/2014 | Egoyants et al. |
| 2014/0338686 A1 | 11/2014 | Plojoux et al. |
| 2016/0286862 A1 | 10/2016 | Silvetrini |

FOREIGN PATENT DOCUMENTS

| | | |
|---|---|---|
| CN | 202375038 U | 8/2012 |
| EP | 0 271 036 A2 | 6/1988 |
| EP | 2 753 201 B1 | 2/2016 |
| RU | 1836039 A3 | 8/1993 |
| WO | WO 2008/121610 A1 | 10/2008 |
| WO | WO 2013/102609 A2 | 7/2013 |
| WO | WO 2015/000974 A1 | 1/2015 |
| WO | WO 2015/197627 A1 | 12/2015 |
| WO | WO 2017/032695 A1 | 3/2017 |

OTHER PUBLICATIONS

Russian Decision to Grant and Search Report, dated Jun. 5, 2020 in corresponding Russian Patent Application No. 2018130723/14(049959) (with English translation), 22 pages.

Chinese Office Action and Search Report dated Aug. 3, 2020 in corresponding Chinese Patent Application No. 201780005532.6 (with English translation), 10 pages.

CARTRIDGE ASSEMBLY HAVING A SLIDING CARTRIDGE BODY

The present invention relates to a cartridge assembly for use in an aerosol-generating system and an aerosol-generating system comprising the cartridge assembly. The present invention finds particular application as a cartridge assembly comprising a nicotine source and an acid source for the generation of an aerosol comprising nicotine salt particles.

Devices for delivering nicotine to a user and comprising a nicotine source and a volatile delivery enhancing compound source are known. For example, WO 2008/121610 A1 discloses devices in which nicotine and a volatile acid, such as pyruvic acid, are reacted with one another in the gas phase to form an aerosol of nicotine salt particles that is inhaled by the user.

In WO 2008/121610 A1 the nicotine source and volatile delivery enhancing compound source may be housed in compartments that are sealed by one or more removable or frangible barriers prior to initial use of the aerosol-generating system.

However, the inclusion of one or more removable or frangible barriers may disadvantageously increase the cost and complexity of manufacturing such aerosol-generating systems. Consequently, it would be desirable to provide a cartridge assembly for use in an aerosol-generating system in which one or more volatile compounds may be retained during storage without the use of removable or frangible barriers.

According to a first aspect of the present invention there is provided a cartridge assembly for use in an aerosol-generating system, the cartridge assembly comprising a cartridge and a mouthpiece. The cartridge comprises a cartridge body comprising a first compartment having a first air inlet and a first air outlet, and a second compartment having a second air inlet and a second air outlet. The cartridge further comprises an enclosure comprising a third air inlet, a third air outlet, a fourth air inlet and a fourth air outlet, wherein the cartridge body is slidably received within the enclosure. The mouthpiece comprises a mouthpiece cavity for receiving the cartridge. The cartridge body is configured to slide with respect to the enclosure from a first position in which the enclosure obstructs each of the first air inlet, the first air outlet, the second air inlet and the second air outlet, to a second position in which the third air inlet is in fluid communication with the first air inlet, the third air outlet is in fluid communication with the first air outlet, the fourth air inlet is in fluid communication with the second air inlet, and the fourth air outlet is in fluid communication with the second air outlet. The cartridge assembly is configured so that insertion of the cartridge into the mouthpiece cavity moves the cartridge body from the first position to the second position.

As used herein with reference to the invention, the term "air inlet" is used to describe one or more apertures through which air may be drawn into a component or portion of a component of the cartridge assembly.

As used herein with reference to the invention, the term "air outlet" is used to describe one or more apertures through which air may be drawn out of a component or portion of a component of the cartridge assembly.

As used herein with reference to the invention, by "obstructed" it is meant that an air inlet or an air outlet is blocked such that airflow through the air inlet or the air outlet is substantially prevented.

Advantageously, a cartridge assembly according to the present invention minimises or substantially prevents the loss of one or more volatile compounds stored within the cartridge assembly before the cartridge assembly is used in an aerosol-generating system. Specifically, the obstruction of the first air inlet, the first air outlet, the second air inlet and the second air outlet by the enclosure when the cartridge body is in the first position may minimise or substantially prevent the loss of one or more volatile compounds stored within the cartridge body.

Advantageously, by using an enclosure to obstruct the air inlets and the air outlets of the cartridge body, the cartridge body being slidable with respect to the enclosure, a cartridge assembly according to the present invention can eliminate the need to use one or more removable or frangible barriers to seal the cartridge body.

Advantageously, a cartridge assembly according to the present invention provides a reliable and consistent means for activating the cartridge. Specifically, the cartridge assembly being configured so that insertion of the cartridge into the mouthpiece cavity moves the cartridge body from the first position to the second position provides automatic activation of the cartridge when the cartridge is inserted into the mouthpiece cavity.

The cartridge body may comprise a first cam surface protruding from the enclosure when the cartridge body is in the first position, wherein the first cam surface engages a first portion of the mouthpiece to move the cartridge body from the first position to the second position when the cartridge is inserted into the mouthpiece cavity. Advantageously, a first cam surface configured to engage a first portion of the mouthpiece may be a simple and cost-effective mechanism for effecting automatic movement of the cartridge body into the second position when the cartridge is inserted into the mouthpiece cavity.

At least one of the first cam surface and the first portion of the mouthpiece may be tapered.

The mouthpiece may define an opening at an end of the mouthpiece cavity for receiving the cartridge. The first cam surface may be tapered and at least part of the first portion of the mouthpiece may define part of an edge of the opening. The first cam surface may be formed by a first protrusion extending from the cartridge body. The first protrusion may comprise a height extending between the cartridge body and the first cam surface, wherein the height of the first protrusion between the cartridge body and the part of the first cam surface in contact with the first portion of the mouthpiece increases as the cartridge is progressively inserted into the mouthpiece cavity.

The cartridge may comprise a single first cam surface formed by a single first protrusion. Preferably the single first protrusion is positioned centrally on a first facet of the cartridge body. Positioning a single first protrusion centrally on a first facet of the cartridge body may advantesgouly facilitate the translation of a sliding motion of the cartridge into the mouthpiece cavity into a sliding motion of the cartridge body with respect to the enclosure. That is, positioning a single first protrusion centrally on a first facet of the cartridge body may advantesgouly prevent the translation of a sliding motion of the cartridge into the mouthpiece into a rotational motion of the cartridge body with respect to the enclosure.

The cartridge may comprise a plurality of first cam surfaces formed by a plurality of first protrusions. In embodiments in which the cartridge comprises a plurality of first protrusions, preferably the plurality of first protrusions are provided on a first facet of the cartridge body. Preferably, the first facet of the cartridge body comprises a line of symmetry, wherein the first protrusions are distributed symmetrically about the line of symmetry. Distributing a plurality of first protrusions symmetrically on a first facet of the cartridge body may facilitate even transmission of force to the cartridge body when the cartridge is inserted into the mouthpiece cavity.

The cartridge assembly is preferably further configured so that removal of the cartridge from the mouthpiece cavity moves the cartridge body from the second position to the first position. Advantageously, such a cartridge assembly provides a reliable and consistent means for deactivating the cartridge. That is, removing the cartridge assembly from the mouthpiece cavity moves the cartridge body into the first position so that the enclosure re-obstructs the first air inlet, the first air outlet, the second air inlet and the second air outlet. This advantageously minimises or substantially prevents loss of any remaining volatile compounds stored within the cartridge body when the cartridge is removed from the mouthpiece cavity. Therefore, such a cartridge assembly may advantageously eliminate the need for a user to consume the entire volatile contents of the cartridge in a single experience, as the cartridge can be removed from the mouthpiece and deactivated after each use.

The cartridge may comprise a resilient component configured to bias the cartridge body into the first position when the cartridge is not received within the mouthpiece cavity. The resilient component may comprise a spring.

Preferably, the cartridge body comprises a second cam surface protruding from the enclosure when the cartridge body is in the second position, wherein the second cam surface engages a second portion of the mouthpiece to move the cartridge body from the second position to the first position when the cartridge is removed from the mouthpiece cavity. Advantageously, a second cam surface configured to engage a second portion of the mouthpiece may be a simple and cost-effective mechanism for effecting automatic movement of the cartridge body into the first position when the cartridge is removed from the mouthpiece cavity.

At least one of the second cam surface and the second portion of the mouthpiece may be tapered.

The second portion of the mouthpiece may comprise a tapered groove formed in an inner surface of the mouthpiece. The mouthpiece may define an opening at an end of the mouthpiece cavity for receiving the cartridge. Preferably, a depth of the tapered groove increases in a direction away from the mouthpiece opening. The tapered groove may be a single tapered groove. The tapered groove may comprise a plurality of tapered grooves. In those embodiments in which the tapered groove comprises a plurality of tapered grooves, preferably the tapered grooves are provided on an internal facet of the mouthpiece. Preferably, the internal facet of the mouthpiece comprises a line of symmetry, wherein the tapered grooves are distributed symmetrically about the line of symmetry. Distributing a plurality of tapered grooves symmetrically on an internal facet of the mouthpiece may facilitate even transmission of force to the cartridge body when the cartridge is removed from the mouthpiece cavity.

The mouthpiece may comprise a slot, wherein at least a part of the second portion of the mouthpiece defines part of an edge of the slot. The slot may comprise a groove formed in an inner surface of the mouthpiece, wherein the groove has a substantially constant depth along its length. The slot may comprise an aperture extending through a wall defining at least part of the mouthpiece cavity. The slot may be a single slot. The slot may comprise a plurality of slots. In those embodiments in which the slot comprises a plurality of slots, preferably the slots are provided on a facet of the mouthpiece. Preferably, the facet of the mouthpiece comprises a line of symmetry, wherein the slots are distributed symmetrically about the one line of symmetry. Distributing a plurality of slots symmetrically on a facet of the mouthpiece may facilitate even transmission of force to the cartridge body when the cartridge is removed from the mouthpiece cavity.

The second cam surface may be formed by a second protrusion extending from the cartridge body. The second protrusion may comprise a height extending between the cartridge body and the second cam surface. The height of the second protrusion may be substantially constant over the entire second cam surface. The height of the second protrusion between the cartridge body and the part of the second cam surface in contact with the second portion of the mouthpiece may increase as cartridge is progressively removed from the mouthpiece cavity. That is, the second cam surface may be tapered. In embodiments in which at least a part of the second portion of the mouthpiece defines part of an edge of a slot, the second cam surface is preferably tapered.

The cartridge may comprise a single second cam surface formed by a single second protrusion. Preferably the single second protrusion is positioned centrally on a second facet of the cartridge body. Positioning a single second protrusion centrally on a second facet of the cartridge body may advantesgouly facilitate the translation of a sliding motion of the cartridge into the mouthpiece cavity into a sliding motion of the cartridge body with respect to the enclosure. That is, positioning a single second protrusion centrally on a second facet of the cartridge body may advantesgouly prevent the translation of a sliding motion of the cartridge into the mouthpiece into a rotational motion of the cartridge body with respect to the enclosure.

The cartridge may comprise a plurality of second cam surfaces formed by a plurality of second protrusions. In embodiments in which the cartridge comprises a plurality of second protrusions, preferably the plurality of second protrusions are provided on a second facet of the cartridge body. Preferably, the second facet of the cartridge body comprises a line of symmetry, wherein the second protrusions are distributed symmetrically about the line of symmetry. Distributing a plurality of second protrusions symmetrically on a second facet of the cartridge body may facilitate even transmission of force to the cartridge body when the cartridge is inserted into the mouthpiece cavity.

Preferably, the number of second protrusions is the same as the number of slots or tapered grooves on the mouthpiece.

The first air inlet and the second air inlet may be positioned at an upstream end of the cartridge body, and the first air outlet and the second air outlet may be positioned at a downstream end of the cartridge body. The enclosure preferably comprises an upstream portion abutting the upstream end of the cartridge body and a downstream portion abutting the downstream end of the cartridge body, the upstream and downstream portions of the enclosure obstructing the air inlets and the air outlets, respectively, of the cartridge body when the cartridge body is in the first position. The third and fourth air inlets are preferably provided in the upstream portion of the enclosure and the third and fourth air outlets are preferably provided in the downstream portion of the enclosure. The enclosure preferably comprises first and second side portions each extending between the upstream and downstream portions so that the enclosure wraps around at least a part of the cartridge body.

The mouthpiece cavity may be configured to slidably receive the cartridge along a first direction, and the cartridge body may be configured to slide with respect to the enclosure from the first position to the second position along a second direction. Preferably, the second direction is substantially orthogonal to the first direction. Configuring the cartridge assembly so that the second direction is substantially orthogonal to the first direction may be particularly preferable in embodiments in which the airflow through the cartridge assembly during use is generally along the first direction. In embodiments in which the cartridge body comprises upstream and downstream ends in which the cartridge body air inlets and air outlets are provided, as described herein, the first direction may extend between the upstream and downstream ends of the cartridge body when the cartridge is inserted into the mouthpiece cavity. In such embodiments, configuring the cartridge assembly so that the second direction is substantially orthogonal to the first direction may advantageously facilitate sliding of the cartridge body with respect to the enclosure while maintaining the necessary contact between the upstream portion of the enclosure and the upstream end of the cartridge body, and while maintaining the necessary contact between the downstream portion of the enclosure and the downstream end of the cartridge body.

In embodiments in which the cartridge body comprises a first cam surface and a second cam surface, preferably the second cam surface is offset in the first direction from the first cam surface.

The cartridge body may be configured to slide with respect to the enclosure from the first position to the second position through a distance of less than about 5 millimetres. Advantageously, configuring the cartridge body to slide through a distance of less than about 5 millimetres may minimise the dimensions of the cartridge assembly while also providing sufficient relative movement between the cartridge body and the enclosure so that the cartridge body air inlets and air outlets are entirely obstructed in the first position and entirely unobstructed in the second position. Preferably, the cartridge body is configured to slide through a distance equal to or greater than the largest dimension of the cartridge body air inlets and air outlets in the direction of movement of the cartridge body relative to the enclosure.

The mouthpiece may comprise a ventilation air inlet providing fluid communication between the exterior of the mouthpiece and the interior of the mouthpiece, wherein the ventilation air inlet is positioned downstream of the cartridge when the cartridge is received within the mouthpiece cavity. The ventilation air inlet may in fluid communication with the mouthpiece cavity and positioned at a downstream end of the mouthpiece cavity.

The cartridge assembly may further comprise a nicotine source positioned within the first compartment and an acid source positioned within the second compartment.

As used herein with reference to the invention, the term "nicotine", is used to describe nicotine, nicotine base or a nicotine salt.

The nicotine source may comprise a first carrier material impregnated with between about 1 milligram and about 50 milligrams of nicotine. The nicotine source may comprise a first carrier material impregnated with between about 1 milligram and about 40 milligrams of nicotine. Preferably, the nicotine source comprises a first carrier material impregnated with between about 3 milligrams and about 30 milligrams of nicotine. More preferably, the nicotine source comprises a first carrier material impregnated with between about 6 milligrams and about 20 milligrams of nicotine. Most preferably, the nicotine source comprises a first carrier material impregnated with between about 8 milligrams and about 18 milligrams of nicotine.

In embodiments in which the first carrier material is impregnated with nicotine base or a nicotine salt, the amounts of nicotine recited herein are the amount of nicotine base or amount of ionised nicotine, respectively.

The first carrier material may be impregnated with liquid nicotine or a solution of nicotine in an aqueous or non-aqueous solvent.

The first carrier material may be impregnated with natural nicotine or synthetic nicotine.

The acid source may comprise an organic acid or an inorganic acid.

Preferably, the acid source comprises an organic acid, more preferably a carboxylic acid, most preferably an alpha-keto or 2-oxo acid or lactic acid.

Advantageously, the acid source comprises an acid selected from the group consisting of 3-methyl-2-oxopentanoic acid, pyruvic acid, 2-oxopentanoic acid, 4-methyl-2-oxopentanoic acid, 3-methyl-2-oxobutanoic acid, 2-oxooctanoic acid, lactic acid and combinations thereof. Advantageously, the acid source comprises pyruvic acid or lactic acid. More advantageously, the acid source comprises lactic acid.

Advantageously, the acid source comprises a second carrier material impregnated with acid.

The first carrier material and the second carrier material may be the same or different.

Advantageously, the first carrier material and the second carrier material have a density of between about 0.1 grams/cubic centimetre and about 0.3 grams/cubic centimetre.

Advantageously, the first carrier material and the second carrier material have a porosity of between about 15 percent and about 55 percent.

The first carrier material and the second carrier material may comprise one or more of glass, cellulose, ceramic, stainless steel, aluminium, polyethylene (PE), polypropylene, polyethylene terephthalate (PET), poly(cyclohexanedimethylene terephthalate) (PCT), polybutylene terephthalate (PBT), polytetrafluoroethylene (PTFE), expanded polytetrafluoroethylene (ePTFE), and BAREX®.

The first carrier material acts as a reservoir for the nicotine.

Advantageously, the first carrier material is chemically inert with respect to nicotine.

The first carrier material may have any suitable shape and size. For example, the first carrier material may be in the form of a sheet or plug.

Advantageously, the shape and size of the first carrier material is similar to the shape and size of the first compartment of the cartridge body.

The shape, size, density and porosity of the first carrier material may be chosen to allow the first carrier material to be impregnated with a desired amount of nicotine.

Advantageously, the first compartment of the cartridge body may further comprise a flavourant. Suitable flavourants include, but are not limited to, menthol.

Advantageously, the first carrier material may be impregnated with between about 3 milligrams and about 12 milligrams of flavourant.

The second carrier material acts as a reservoir for the acid.

Advantageously, the second carrier material is chemically inert with respect to the acid.

The second carrier material may have any suitable shape and size. For example, the second carrier material may be in the form of a sheet or plug.

Advantageously, the shape and size of the second carrier material is similar to the shape and size of the second compartment of the cartridge body.

The shape, size, density and porosity of the second carrier material may be chosen to allow the second carrier material to be impregnated with a desired amount of acid.

Advantageously, acid source is a lactic acid source comprising a second carrier material impregnated with between about 2 milligrams and about 60 milligrams of lactic acid.

Preferably, the lactic acid source comprises a second carrier material impregnated with between about 5 milligrams and about 50 milligrams of lactic acid. More preferably, the lactic acid source comprises a second carrier material impregnated with between about 8 milligrams and about 40 milligrams of lactic acid. Most preferably, the lactic acid source comprises a second carrier material impregnated with between about 10 milligrams and about 30 milligrams of lactic acid.

The shape and dimensions of the first compartment of the cartridge body may be chosen to allow a desired amount of nicotine to be housed in the cartridge body.

The shape and dimensions of the second compartment of the cartridge body may be chosen to allow a desired amount of acid to be housed in the cartridge body.

The ratio of nicotine and acid required to achieve an appropriate reaction stoichiometry may be controlled and balanced through variation of the volume of the first compartment relative to the volume of the second compartment.

The first air inlet of the first compartment of the cartridge body and the second air inlet of the second compartment of the cartridge body may each comprise one or more apertures. For example, the first air inlet of the first compartment of the cartridge body and the second air inlet of the second compartment of the cartridge body may each comprise one, two, three, four, five, six or seven apertures.

The first air inlet of the first compartment of the cartridge body and the second air inlet of the second compartment of the cartridge body may comprise the same or different numbers of apertures.

Advantageously, the first air inlet of the first compartment of the cartridge body and the second air inlet of the second compartment of the cartridge body each comprise a plurality of apertures. For example, the first air inlet of the first compartment of the cartridge body and the second air inlet of the second compartment of the cartridge body may each comprise two, three, four, five, six or seven apertures.

Providing a first compartment having a first air inlet comprising a plurality of apertures and a second compartment having a second air inlet comprising a plurality of apertures may advantageously result in more homogeneous airflow within the first compartment and the second compartment, respectively. In use, this may improve entrainment of nicotine in an air stream drawn through the first compartment and improve entrainment of acid in an air stream drawn through the second compartment.

The ratio of nicotine and acid required to achieve an appropriate reaction stoichiometry may be controlled and balanced through variation of the volumetric airflow through the first compartment of the cartridge body relative to the volumetric airflow through the second compartment of the cartridge body. The ratio of the volumetric airflow through the first compartment relative to the volumetric airflow through the second compartment may be controlled through variation of one or more of the number, dimensions and location of the apertures forming the first air inlet of the first compartment of the cartridge body relative to the number, dimensions and location of the apertures forming the second air inlet of the second compartment of the cartridge body.

In embodiments in which the acid source comprises lactic acid, advantageously the flow area of the second air inlet of the second compartment of the cartridge body is greater than the flow area of the first air inlet of the first compartment of the cartridge body.

As used herein with reference to the invention, the term "flow area" is used to describe the cross-sectional area of an air inlet or air outlet through which airflows during use. In embodiments in which an air inlet or air outlet comprises a plurality of apertures, the flow area of the air inlet or air outlet is the total flow area of the air inlet or air outlet and is equal to the sum of the flow areas of each of the plurality of apertures forming the air inlet or air outlet. In embodiments in which the cross-sectional area of an air inlet or air outlet varies in the direction of airflow, the flow area of the air inlet or air outlet is the minimum cross-sectional area in the direction of airflow.

Increasing the flow area of the second air inlet of the second compartment of the cartridge body relative to the flow area of the first air inlet of the first compartment of the cartridge body advantageously increases the volumetric airflow through the second air inlet compared to the volumetric airflow through the first air inlet.

In embodiments in which the acid source comprises lactic acid, preferably the ratio of the flow area of the first air inlet of the first compartment of the cartridge body to the flow area of the second air inlet of the second compartment of the cartridge body is between about 3:4 and about 1:2. More preferably, the ratio of the flow area of the first air inlet of the first compartment of the cartridge body to the flow area of the second air inlet of the second compartment of the cartridge body is between about 2:3 and about 1:2.

The flow area of the second air inlet of the second compartment of the cartridge body may be increased relative to the flow area of the first air inlet of the first compartment of the cartridge body by one or both of increasing the size of the one or more apertures forming the second air inlet relative to the size of the one or more apertures forming the first air inlet and increasing the number of apertures forming the second air inlet relative to the number of apertures forming the first air inlet.

Advantageously, the flow area of the second air inlet of the second compartment of the cartridge body is increased relative to the flow area of the first air inlet of the first compartment of the cartridge body by increasing the number of apertures forming the second air inlet relative to the number of apertures forming the first air inlet.

Advantageously, the first air inlet of the first compartment of the cartridge body comprises between 2 and 5 apertures.

Advantageously, the second air inlet of the second compartment of the cartridge body comprises between 3 and 7 apertures.

Advantageously, the flow area of the first air inlet of the first compartment of the cartridge body is between about 0.1 square millimetres and about 1.6 square millimetres, more advantageously between about 0.2 square millimetres and about 0.8 square millimetres.

In embodiments in which the first air inlet of the first compartment of the cartridge body comprises a plurality of apertures, the apertures may have different flow areas so that the flow area of the first air inlet of the first compartment of the cartridge body is divided unequally between the apertures forming the first air inlet.

In embodiments in which the first air inlet of the first compartment of the cartridge body comprises a plurality of apertures, each of the apertures may have the same flow area so that the flow area of the first air inlet of the first compartment of the cartridge body is divided equally between the apertures forming the first air inlet. Providing a first compartment having a first air inlet comprising a plurality of apertures having substantially the same flow area may advantageously simplify manufacturing of the cartridge body.

The first air inlet of the first compartment of the cartridge body may comprise one or more apertures having any suitable cross-sectional shape. For example, the cross-sectional shape of each aperture may be circular, elliptical, square or rectangular. Advantageously, each aperture has a substantially circular cross-sectional shape. Advantageously, the diameter of each aperture is between about 0.2 millimetres and about 0.6 millimetres.

In embodiments in which the acid source comprises lactic acid, advantageously the flow area of the second air inlet of the second compartment of the cartridge body is between about 0.2 square millimetres and about 2.4 square millimetres, more advantageously between about 0.4 square millimetres and about 1.2 square millimetres.

In embodiments in which the second air inlet of the second compartment of the cartridge body comprises a plurality of apertures, the apertures may have different flow areas so that the total flow area of the second air inlet of the second compartment of the cartridge body is divided unequally between the apertures forming the second air inlet.

In embodiments in which the second air inlet of the second compartment of the cartridge body comprises a plurality of apertures, each of the apertures may have the same flow area so that the total flow area of the second air inlet of the second compartment of the cartridge body is divided equally between the apertures forming the second air inlet. Providing a second compartment having a second air inlet comprising a plurality of apertures having substantially the same flow area may advantageously simplify manufacturing of the cartridge body.

The second air inlet of the second compartment of the cartridge body may comprise one or more apertures having any suitable cross-sectional shape. For example, the cross-sectional shape of each aperture may be circular, elliptical, square or rectangular. Advantageously, each aperture has a substantially circular cross-sectional shape. Advantageously, the diameter of each aperture is between about 0.2 millimetres and about 0.6 millimetres.

The first air outlet of the first compartment of the cartridge body and the second air outlet of the second compartment of the cartridge body may each comprise one or more apertures. For example, the first air outlet of the first compartment of the cartridge body and the second air outlet of the second compartment of the cartridge body may each comprise one, two, three, four, five, six or seven apertures.

The first air outlet of the first compartment of the cartridge body and the second air outlet of the second compartment of the cartridge body may comprise the same or different numbers of apertures.

Advantageously, the first air outlet of the first compartment of the cartridge body and the second air outlet of the second compartment of the cartridge body each comprises a plurality of apertures. For example, the first air outlet of the first compartment of the cartridge body and the second air outlet of the second compartment of the cartridge body may each comprise two, three, four, five, six or seven apertures. Providing a first compartment having a first air outlet comprising a plurality of apertures and a second compartment having a second air outlet comprising a plurality of apertures may advantageously result in more homogeneous airflow within the first compartment and the second compartment, respectively. In use, this may improve entrainment of nicotine in an air stream drawn through the first compartment and improve entrainment of acid in an air stream drawn through the second compartment.

In embodiments in which the first air outlet of the first compartment of the cartridge body comprises a plurality of apertures, advantageously the first air outlet comprises between 2 and 5 apertures.

In embodiments in which the second air outlet of the second compartment of the cartridge body comprises a plurality of apertures, advantageously, the second air outlet comprises between 3 and 7 apertures.

Advantageously, the first air outlet of the first compartment of the cartridge body and the second air outlet of the second compartment of the cartridge body each comprises a single aperture. Providing a first compartment having a first air outlet comprising a single aperture and a second compartment having a second air outlet comprising a single aperture may advantageously simplify manufacturing of the cartridge body.

The ratio of nicotine and acid required to achieve an appropriate reaction stoichiometry may be controlled and balanced through variation of the volumetric airflow through the first compartment of the cartridge body relative to the volumetric airflow through the second compartment of the cartridge body. The ratio of the volumetric airflow through the first compartment relative to the volumetric airflow through the second compartment may be controlled through variation of one or more of the number, dimensions and location of the apertures forming the first air outlet of the first compartment of the cartridge body relative to the number, dimensions and location of the apertures forming the second air outlet of the second compartment of the cartridge body.

The flow area of the first air outlet of the first compartment may be the same as or different to the flow area of the second air outlet of the second compartment.

The flow area of the second air outlet of the second compartment of the cartridge body may be greater than flow area of the first air outlet of the first compartment of the cartridge body.

Increasing the flow area of the second air outlet of the second compartment of the cartridge body relative to the flow area of the first air outlet of the first compartment of the cartridge body may advantageously increase the volumetric airflow through the second air outlet compared to the volumetric airflow through the first air outlet.

In embodiments in which the acid source comprises lactic acid, the ratio of the flow area of the first air outlet of the first compartment of the cartridge body to the flow area of the second air outlet of the second compartment of the cartridge body is preferably between about 3:4 and about 1:2. More preferably, the ratio of the flow area of the first air outlet of the first compartment of the cartridge body to the flow area of the second air outlet of the second compartment of the cartridge body is between about 2:3 and about 1:2.

In embodiments in which the flow area of the second air outlet of the second compartment of the cartridge body is greater than flow area of the first air outlet of the first compartment of the cartridge body, the flow area of the second air outlet of the second compartment of the cartridge body may be increased relative to the flow area of the first air outlet of the first compartment of the cartridge body by one or both of increasing the size of the one or more apertures forming the second air outlet relative to the size of the one or more apertures forming the first air outlet and increasing the number of apertures forming the second air outlet relative to the number of apertures forming the first air outlet.

Advantageously, the flow area of the second air outlet of the second compartment of the cartridge body is increased relative to the flow area of the first air outlet of the first compartment of the cartridge body by increasing the number of apertures forming the second air outlet relative to the number of apertures forming the first air outlet.

The first air inlet and the first air outlet of the first compartment of the cartridge body may comprise the same or different numbers of apertures.

Advantageously, the first air inlet and the first air outlet of the first compartment of the cartridge body comprise the same numbers of apertures. Providing a first compartment having a first air inlet and a first air outlet comprising the same number of apertures may advantageously simplify manufacturing of the cartridge body.

The second air inlet and the second air outlet of the second compartment of the cartridge body may comprise the same or different numbers of apertures.

Advantageously, the second air inlet and the second air outlet of the second compartment of the cartridge body comprise the same numbers of apertures. Providing a second compartment having a second air inlet and a second air outlet comprising the same number of apertures may advantageously simplify manufacturing of the cartridge body.

Advantageously, the flow area of the first air outlet of the first compartment of the cartridge body is between about 0.1 square millimetres and about 5 square millimetres.

In embodiments in which the first air outlet of the first compartment of the cartridge body comprises a plurality of apertures, the apertures may have different flow areas so that the flow area of the first air outlet of the first compartment of the cartridge body is divided unequally between the apertures forming the first air outlet.

In embodiments in which the first air outlet of the first compartment of the cartridge body comprises a plurality of apertures, each of the apertures may have the same flow area so that the flow area of the first air outlet of the first compartment of the cartridge body is divided equally between the apertures forming the first air outlet. Providing a first compartment having a first air outlet comprising a plurality of apertures having substantially the same flow area may advantageously simplify manufacturing of the cartridge body.

The first air outlet of the first compartment of the cartridge body may comprise one or more apertures having any suitable cross-sectional shape. For example, the cross-sectional shape of each aperture may be circular, elliptical, square or rectangular. In embodiments in which the first air outlet of the first compartment of the cartridge body comprises a plurality of apertures, advantageously each aperture has a substantially circular cross-sectional shape. In such embodiments, advantageously the diameter of each aperture is between about 0.2 millimetres and about 0.6 millimetres.

The dimensions of the one or more apertures forming the first air inlet of the first compartment of the cartridge body may be the same as or different to the dimensions of the one or more apertures forming the first air outlet of the first compartment of the cartridge body.

Advantageously, the dimensions of the one or more apertures forming the first air inlet of the first compartment of the cartridge body is substantially the same as the dimensions of the one or more apertures forming the first air outlet of the first compartment of the cartridge body. Providing a first compartment having a first air inlet and a first air outlet comprising one or more apertures of substantially the same dimensions may advantageously simplify manufacturing of the cartridge body.

Advantageously, the dimensions of the one or more apertures forming the first air outlet of the first compartment of the cartridge body are greater than the dimensions of the one or more apertures forming the first air inlet of the first compartment of the cartridge body. Increasing the dimensions of the apertures forming the first air outlet of the first compartment of the cartridge body relative to the dimensions of the apertures forming the first air inlet of the first compartment of the cartridge body may advantageously reduce the risk of the first air outlet of the first compartment of the cartridge body becoming obstructed by, for example, dust.

Advantageously, the flow area of the second air outlet of the second compartment of the cartridge body is between about 0.1 square millimetres and about 5 square millimetres.

In embodiments in which the second air outlet of the second compartment of the cartridge body comprises a plurality of apertures, the apertures may have different flow areas so that the total flow area of the second air outlet of the second compartment of the cartridge body is divided unequally between the apertures forming the second air outlet.

In embodiments in which the second air outlet of the second compartment of the cartridge body comprises a plurality of apertures, each of the apertures may have the same flow area so that the total flow area of the second air outlet of the second compartment of the cartridge body is divided equally between the apertures forming the second air outlet. Providing a second compartment having a second air outlet comprising a plurality of apertures having substantially the same flow area may advantageously simplify manufacturing of the cartridge body.

The second air outlet of the second compartment of the cartridge body may comprise one or more apertures having any suitable cross-sectional shape. For example, the cross-sectional shape of each aperture may be circular, elliptical, square or rectangular. In embodiments in which the second air outlet of the second compartment of the cartridge body comprises a plurality of apertures, advantageously each aperture has a substantially circular cross-sectional shape. In such embodiments, advantageously the diameter of each aperture is between about 0.2 millimetres and about 0.6 millimetres.

The dimensions of the one or more apertures forming the second air inlet of the second compartment of the cartridge body may be the same as or different to the dimensions of the one or more apertures forming the second air outlet of the second compartment of the cartridge body.

Advantageously, the dimensions of the one or more apertures forming the second air inlet of the second compartment of the cartridge body are substantially the same as the dimensions of the one or more apertures forming the second air outlet of the second compartment of the cartridge body. Providing a second compartment having a second air inlet and a second air outlet comprising one or more apertures of substantially the same dimensions may advantageously simplify manufacturing of the cartridge body.

Advantageously, the dimensions of the one or more apertures forming the second air outlet of the second compartment of the cartridge body are greater than the dimensions of the one or more apertures forming the second air inlet of the second compartment of the cartridge body. Increasing the dimensions of the apertures forming the second air outlet of the second compartment of the cartridge body relative to the dimensions of the apertures forming the second air inlet of the second compartment of the cartridge body may advantageously reduce the risk of the second air outlet of the second compartment of the cartridge body becoming obstructed by, for example, dust.

In embodiments in which the cartridge assembly comprises a nicotine source positioned within the first compartment and an acid source positioned within the second compartment, nicotine vapour released from the nicotine source in the first compartment of the cartridge and acid vapour released from the acid source in the second compartment of the cartridge may react with one another in the gas phase in the mouthpiece to form an aerosol of nicotine salt particles.

The cartridge assembly may comprise one or more aerosol-modifying agents positioned within the mouthpiece. For example, mouthpiece may contain one or more sorbents, one or more flavourants, one or more chemesthetic agents or a combination thereof.

The first compartment and the second compartment may be arranged symmetrically with respect to each other within the cartridge body.

Advantageously, the cartridge is an elongate cartridge. In embodiments in which the cartridge is an elongate cartridge, the first compartment and the second compartment of the cartridge body may be arranged symmetrically about the longitudinal axis of the cartridge.

The cartridge may have any suitable transverse cross-sectional shape. For example, the transverse cross-sectional shape of the cartridge may be circular, semi-circular, elliptical, triangular, square, rectangular or trapezoidal. Preferably, the transverse cross-sectional shape of the cartridge is square or rectangular.

The cartridge may have any suitable size.

For example, the cartridge may have a length of between about 5 millimetres and about 50 millimetres. Advantageously, the cartridge may have a length between about 10 millimetres and about 20 millimetres.

For example, the cartridge may have a width of between about 4 millimetres and about 10 millimetres and a height of between about 4 millimetres and about 10 millimetres. Advantageously, the cartridge may have a width of between about 6 millimetres and about 8 millimetres and a height of between about 6 millimetres and about 8 millimetres.

The cartridge body, the enclosure and the mouthpiece may be formed from any suitable material or combination of materials. Suitable materials include, but are not limited to, aluminium, polyether ether ketone (PEEK), polyimides, such as Kapton®, polyethylene terephthalate (PET), polyethylene (PE), high-density polyethylene (HDPE), polypropylene (PP), polystyrene (PS), fluorinated ethylene propylene (FEP), polytetrafluoroethylene (PTFE), polyoxymethylene (POM), epoxy resins, polyurethane resins, vinyl resins, liquid crystal polymers (LCP) and modified LCPs, such as LCPs with graphite or glass fibres.

The cartridge body, the enclosure and the mouthpiece may be formed from the same or different materials.

The cartridge body may be formed from one or more materials that are nicotine-resistant and acid-resistant.

The first compartment of the cartridge body may be coated with one or more nicotine-resistant materials and the second compartment of the cartridge body may be coated with one or more acid-resistant materials.

Examples of suitable nicotine-resistant materials and acid-resistant materials include, but are not limited to, polyethylene (PE), polypropylene (PP), polystyrene (PS), fluorinated ethylene propylene (FEP), polytetrafluoroethylene (PTFE), epoxy resins, polyurethane resins, vinyl resins and combinations thereof.

Use of one or more nicotine-resistant materials to one or both of form the cartridge body and coat the interior of the first compartment of the cartridge body may advantageously enhance the shelf life of the cartridge.

Use of one or more acid-resistant materials to one or both of form the cartridge body and coat the interior of the second compartment of the cartridge body may advantageously enhance the shelf life of the cartridge.

The cartridge assembly may comprise a heater configured to heat the first compartment and the second compartment. In such embodiments, the heater is advantageously located between the first compartment and the second compartment. That is the first compartment and the second compartment are disposed on either side of the heater.

The heater may be an electrical heater. The heater may be a resistive heater.

Advantageously, the heater is configured to heat the first compartment and the second compartment of the cartridge body to a temperature of below about 250 degrees Celsius. Preferably, the heater is configured to heat the first compartment and the second compartment of the cartridge body to a temperature of between about 80 degrees Celsius and about 150 degrees Celsius.

Advantageously, the heater is configured to heat the first compartment and the second compartment of the cartridge body to substantially the same temperature.

As used herein with reference to the invention, by "substantially the same temperature" it is meant that the difference in temperature between the first compartment and the second compartment of the cartridge body measured at corresponding locations relative to the heater is less than about 3° C.

The cartridge body may comprise a third compartment for receiving a heating element of an aerosol-generating device. Preferably, the third compartment is positioned between the first compartment and the second compartment. That is, the first compartment and the second compartment are disposed on either side of the third compartment. Preferably, the enclosure comprises an aperture aligned with the third compartment when the cartridge body is in the second position. In use, a heating element of an aerosol-generating device is received within the third compartment to heat the first compartment and the second compartment.

The cartridge may comprise a susceptor for inductively heating the first compartment and the second compartment. In such embodiments, the susceptor is advantageously located between the first compartment and the second compartment. That is, the first compartment and the second compartment are disposed on either side of the susceptor.

In use, heating the first compartment and the second compartment of the cartridge body to a temperature above ambient temperature advantageously enables control of the vapour concentrations of volatile compounds stored within the first and second compartments. For example, in embodiments in which the cartridge assembly comprises a nicotine source positioned within the first compartment and an acid source positioned within the second compartment, heating the first and second compartments enables the vapour pressure of nicotine in the first compartment and the vapour pressure of acid in the second compartment to be controlled and balanced proportionally to yield an efficient reaction stoichiometry between the nicotine and the acid. Advantageously, this may improve the efficiency of the formation of nicotine salt particles and the consistency of delivery to a user. Advantageously, it may also reduce the delivery of unreacted nicotine and unreacted acid to a user.

The cartridge body may be formed from one or more thermally conductive materials.

The first compartment of the cartridge body and the second compartment of the cartridge body may be coated with one or more thermally conductive materials.

Use of one or more thermally conductive materials to one or both of form the cartridge body and coat the interior of the first compartment and the second compartment of the cartridge body may advantageously increase heat transfer from a heater or a susceptor to the nicotine source and the acid source.

Suitable thermally conductive materials include, but are not limited to, metals such as, for example, aluminium, chromium, copper, gold, iron, nickel and silver, alloys, such as brass and steel and combinations thereof.

The cartridge body may be formed of one or more materials having a low resistivity or a high resistivity depending on whether the first compartment and the second compartment are heated by conduction or induction.

The first compartment of the cartridge body and the second compartment of the cartridge body may be coated with one or more materials having a low resistivity or a high resistivity depending on whether the first compartment and the second compartment are heated by conduction or induction.

The cartridge body may be formed by any suitable method. Suitable methods include, but are not limited to, deep drawing, injection moulding, blistering, blow forming and extrusion.

The cartridge may be designed to be disposed of once the nicotine in the first compartment and the acid in the second compartment are depleted.

The cartridge may be designed to be refillable.

The mouthpiece may be designed to be disposed of once the nicotine in the first compartment and the acid in the second compartment are depleted.

The mouthpiece may be designed to be reusable. In embodiments in which the mouthpiece is designed to be reusable, the cartridge is advantageously configured to be removable from the mouthpiece cavity.

The cartridge assembly may simulate the shape and dimensions of a combustible smoking article, such as a cigarette, a cigar, or a cigarillo. Advantageously, in such embodiments the cartridge assembly may simulate the shape and dimensions of a cigarette.

The cartridge assembly may be configured for engagement with the housing of an aerosol-generating device. Preferably, at least one of the cartridge and the mouthpiece is configured for engagement with the housing of an aerosol-generating device.

According to a second aspect of the present invention there is provided an aerosol-generating system comprising an aerosol-generating device and a cartridge assembly according to the first aspect of the present invention, in accordance with any of the embodiments described herein. The aerosol-generating device comprises a device cavity configured to receive an upstream end of the cartridge assembly and a heater for heating the first compartment and the second compartment of the cartridge body.

In those embodiments in which the cartridge body comprises a third compartment for receiving a heating element, the heater of the aerosol-generating device advantageously comprises a heating element positioned within the device cavity and configured to be received within the third compartment of the cartridge body when the upstream end of the cartridge assembly is received within the device cavity. The heating element may be a resistive heating element. In use, the heating element is received within the third compartment and heats the first compartment and the second compartment.

In those embodiments in which the cartridge body comprises a susceptor positioned between the first compartment and the second compartment, the heater of the aerosol-generating device advantageously comprises an inductive heater surrounding at least a portion of the device cavity. In use, the inductive heater inductively heats the susceptor, which heats the first compartment and the second compartment.

Advantageously, the heater of the aerosol-generating device is configured to heat the first compartment and the second compartment of the cartridge body to a temperature of below about 250 degrees Celsius. Preferably, the heater of the aerosol-generating device is configured to heat the first compartment and the second compartment of the cartridge body to a temperature of between about 80 degrees Celsius and about 150 degrees Celsius.

Advantageously, the heater of the aerosol-generating device is configured to heat the first compartment and the second compartment of the cartridge body to substantially the same temperature.

The aerosol-generating device may further comprise a power supply for supplying power to the heater and a controller configured to control a supply of power from the power supply to the heater.

The aerosol-generating device may comprise one or more temperature sensors configured to sense the temperature of at least one of the heater, the first compartment, and the second compartment. In such embodiments, the controller may be configured to control a supply of power to the heater based on a sensed temperature.

For the avoidance of doubt, features described above in relation to one aspect of the invention may also be applicable to other aspects of the invention. In particular, features described above in relation to the cartridge assembly of the invention may also relate, where appropriate, to the aerosol-generating systems of the invention, and vice versa.

Embodiments of the invention will now be described, by way of example only, with reference to the accompanying drawings, in which.

Figure 1:
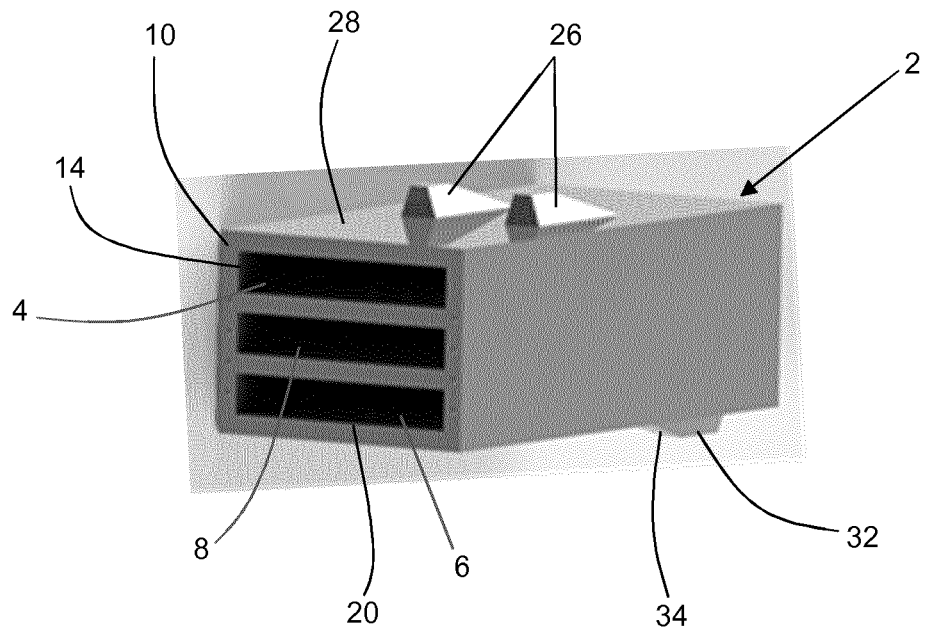
FIG. 1 shows a first perspective view of a cartridge body in accordance with an embodiment of the present invention.
Figure 2:
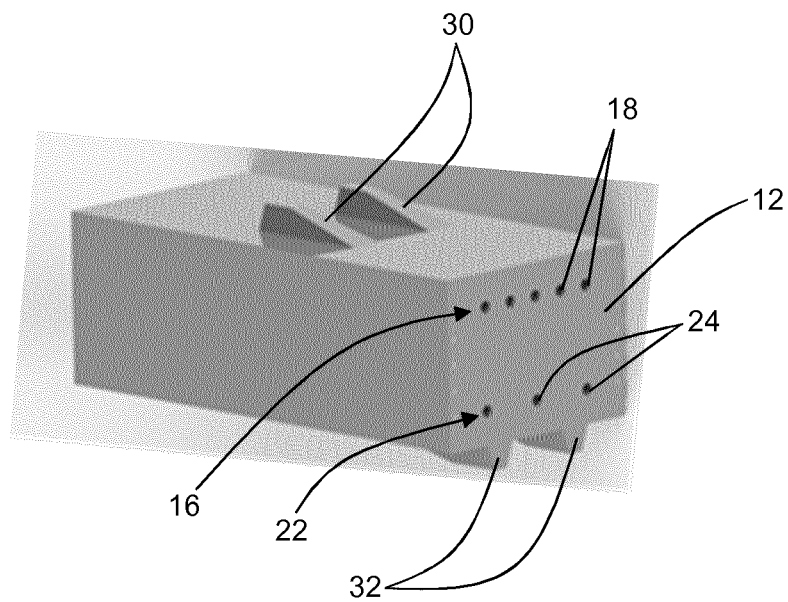
FIG. 2 shows a second perspective view of the cartridge body of FIG. 1.

FIGS. 1 and 2 show a cartridge body 2 in accordance with an embodiment of the present invention. The cartridge body 2 comprises a first compartment 4 housing a nicotine source, a second compartment 6 housing an acid source, and a third compartment 8 positioned between the first and second compartments 4, 6. The third compartment 8 may be configured to receive a heating element of an aerosol-generating device. Alternatively, a susceptor may be housed in the third compartment 8 for heating the first and second compartments 4, 6 via inductive heating of the susceptor using an inductive heater of an aerosol-generating device.

The cartridge body 8 comprises an upstream end 10 and a downstream end 12. The first compartment 4 comprises a first air inlet 14 at the upstream end 10 of the cartridge body 2 and a first air outlet 16 at the downstream end 12 of the cartridge body 2. The first air outlet 16 comprises a row of first outlet apertures 18.

The second compartment 6 comprises a second air inlet 20 at the upstream end 10 of the cartridge body 2 and a second air outlet 22 at the downstream end 12 of the cartridge body 2. The second air outlet 22 comprises a row of second outlet apertures 24.

The cartridge body 2 further comprises a pair of first protrusions 26 extending from a top surface 28 of the cartridge body 2, each of the first protrusions 26 defining a tapered first cam surface 30. The cartridge body 2 also comprises a pair of second protrusions 32 extending from a bottom surface of the cartridge body 2, each of the second protrusions 32 defining a tapered second cam surface 34.

Figure 3:
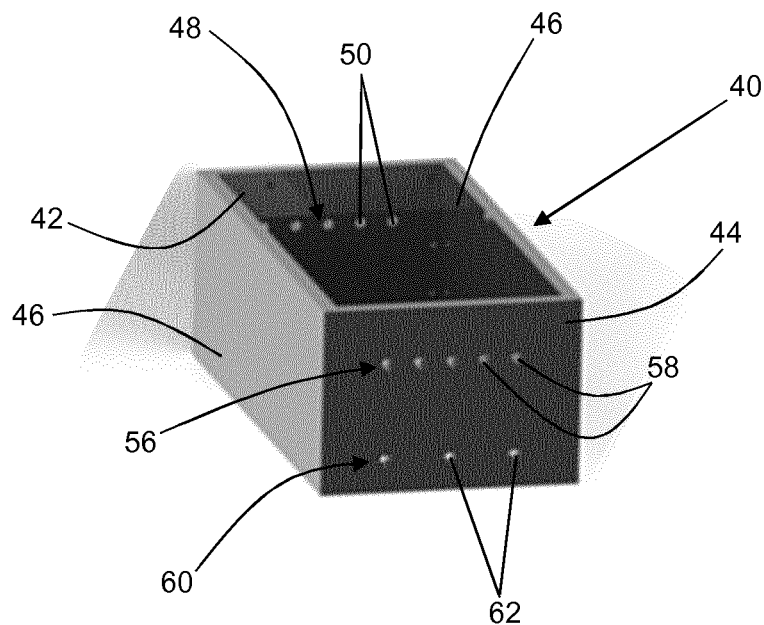
FIG. 3 shows an enclosure in accordance with an embodiment of the present invention.

FIG. 3 shows an enclosure 40 in accordance with an embodiment of the present invention. The enclosure 40 comprises an upstream portion 42, a downstream portion 44 and two side portions 46. A third air inlet 48 comprising a row of third inlet apertures 50 and a fourth air inlet 52 comprising a row of fourth inlet apertures 54 are provided in the upstream portion 42 of the enclosure 40. A third air outlet 56 comprising a row of third outlet apertures 58 and a fourth air outlet 60 comprising a row of fourth outlet apertures 62 are provided in the downstream portion 44 of the enclosure 40.

Figure 4:
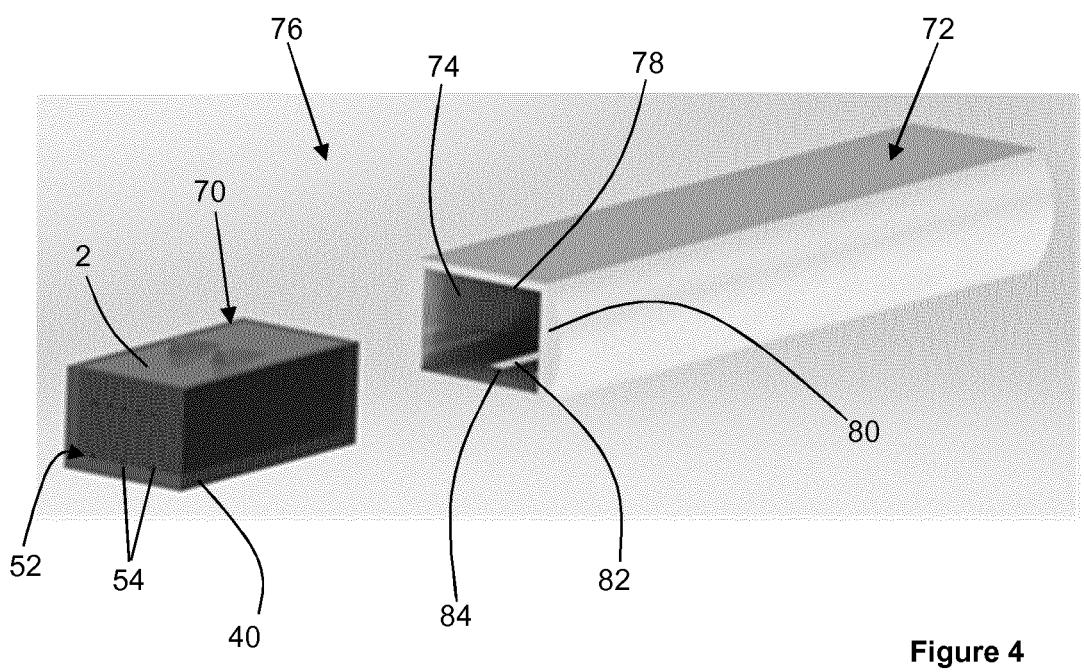
FIG. 4 shows a cartridge assembly in accordance with an embodiment of the present invention.

FIG. 4 shows the cartridge body 2 of FIGS. 1 and 2 combined with the enclosure 40 of FIG. 3 to form a cartridge 70. The cartridge body 2 is slidably received within the enclosure 40 and is retained within the enclosure 40 by an interference fit. FIG. 4 also shows a mouthpiece 72 comprising a mouthpiece cavity 74 for receiving the cartridge 70. The combination of the cartridge 70 and the mouthpiece 72 forms a cartridge assembly 76.

The mouthpiece 72 further comprises an opening 78 for receiving the cartridge 70 into the mouthpiece cavity 74, the opening 78 positioned at an upstream end 80 of the mouthpiece 72. The mouthpiece 72 also comprises a pair of slots 82 provided in a bottom of the mouthpiece cavity 74. As will be further described with reference to FIGS. 5 and 6, a top edge of the opening 78 interacts with the tapered first cam surfaces 30 of the cartridge body 2 when the cartridge 70 is inserted into the mouthpiece cavity 74. As will be further described with reference to FIGS. 5 and 6, an upstream edge 84 of each slot 82 interacts with the corresponding tapered second cam surface 34 of the cartridge body 2 when the cartridge 70 is removed from the mouthpiece cavity 74.

The mouthpiece 72 further comprises a mouthpiece air outlet (not shown) positioned at a downstream end of the mouthpiece and in fluid communication with the mouthpiece cavity 74. In use, a user draws on the downstream end of the mouthpiece 72 to draw air through the first and second compartments 4, 6 of the cartridge body 2, through the mouthpiece 72 and out through the mouthpiece air outlet. Nicotine vapour from the first compartment 4 and acid vapour from the second compartment 6 react in the gas phase in a downstream end of the mouthpiece cavity 74 to form an aerosol of nicotine salt particles for delivery to the user.

Figure 5:
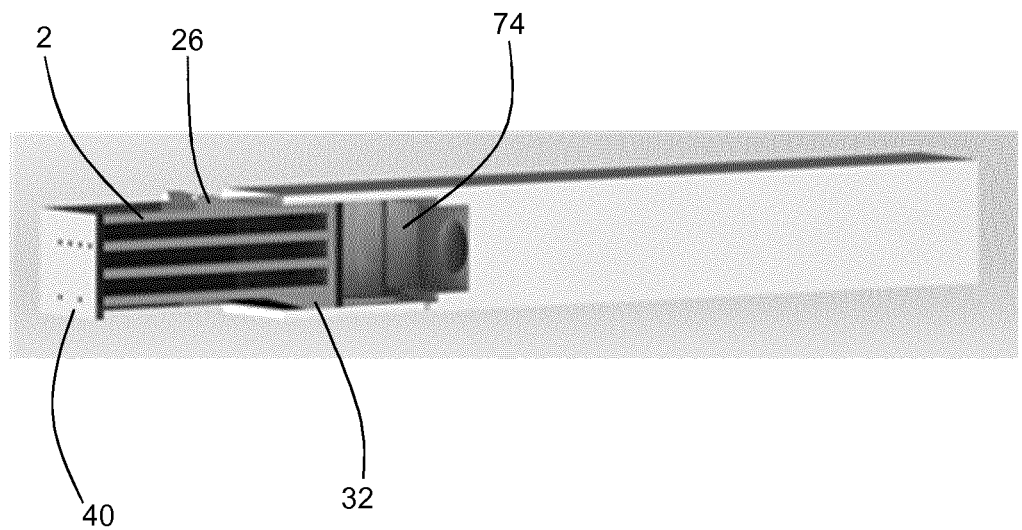
FIG. 5 shows the cartridge assembly of FIG. 4 with the cartridge partially inserted into the mouthpiece.
Figure 6:
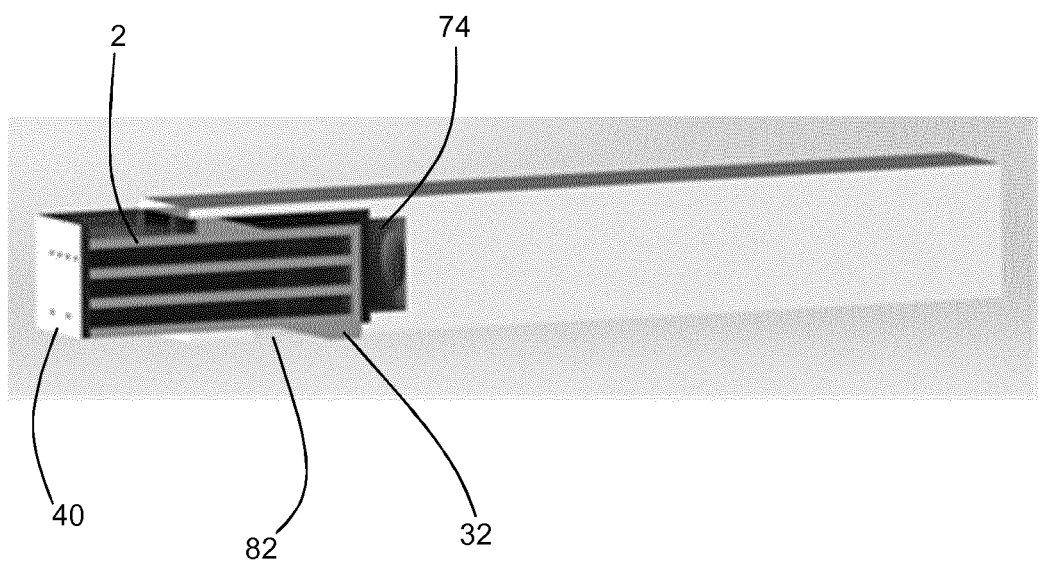
FIG. 6 shows the cartridge assembly of FIG. 4 with the cartridge fully inserted into the mouthpiece.

FIGS. 5 and 6 show a cross-sectional view of the cartridge assembly 76 to illustrate the insertion and removal of the cartridge 70 into and from the mouthpiece cavity 74. As shown in FIGS. 4 and 5, before the cartridge 70 is inserted into the mouthpiece cavity 74, the cartridge body 2 is positioned within the enclosure 40 in a first position. In the first position, the enclosure 40 obstructs the first air inlet 14, the second air inlet 20, the first air outlet 16 and the second air outlet 22 of the cartridge body 2 to substantially prevent the loss of nicotine vapour and acid vapour from the first and second compartments 4, 6 respectively.

When the cartridge 70 is inserted into the mouthpiece cavity 74, the tapered first cam surfaces 30 of the first protrusions 26 interact with a top edge of the mouthpiece opening 78. A height of the enclosure 40 is substantially the same as the height of the mouthpiece cavity 74 so that the interaction between the tapered first cam surface 30 and the top edge of the mouthpiece opening 78 slides the cartridge body 2 downward with respect to the enclosure 40. As the cartridge 70 is progressively inserted into the mouthpiece cavity 70 the cartridge body 2 slides progressively with respect to the enclosure 40 until the cartridge 70 is fully inserted into the mouthpiece cavity 74 and the cartridge body 2 slides into the second position with respect to the enclosure 40, as shown in FIG. 6. In the second position, the third air inlet 48 is in fluid communication with the first air inlet 14, the third air outlet 56 is in fluid communication with the first air outlet 16, the fourth air inlet 52 is in fluid communication with the second air inlet 20, and the fourth air outlet 60 is in fluid communication with the second air outlet 22 so that an air flow path is created through each of the first and second compartments 4, 6. As the cartridge body 2 moves into the second position, the second protrusions are received into the respective slots 82 in the mouthpiece cavity 74.

When the cartridge 70 is removed from the mouthpiece cavity 74, the tapered second cam surface 34 of each second protrusion 32 interacts with the front edge 84 of the respective slot 82 in the mouthpiece cavity 74 to slide the cartridge body 2 upward with respect to the enclosure 40. As the cartridge 70 is progressively removed from the mouthpiece cavity 70 the cartridge body 2 slides progressively with respect to the enclosure 40 until the cartridge body 2 slides into the first position with respect to the enclosure 40, as shown in FIG. 5. In the first position, the enclosure 40 obstructs the first air inlet 14, the second air inlet 20, the first air outlet 16 and the second air outlet 22 of the cartridge body 2 to substantially prevent the loss of nicotine vapour and acid vapour from the first and second compartments 4, 6. The cartridge 70 may be repeatedly inserted into and removed from the mouthpiece cavity 74 so that nicotine vapour and acid vapour are released from the first and second compartments 4, 6 only when the cartridge 70 is inserted into the mouthpiece cavity 74 and the cartridge assembly 76 is being used.

The invention claimed is:

1. A cartridge assembly for an aerosol-generating system, the cartridge assembly comprising:
    a cartridge comprising:
        a cartridge body comprising a first compartment having a first air inlet and a first air outlet, and further comprising a second compartment having a second air inlet and a second air outlet, and
        an enclosure comprising a third air inlet, a third air outlet, a fourth air inlet, and a fourth air outlet, wherein the cartridge body is slidably received within the enclosure; and
    a mouthpiece comprising a mouthpiece cavity configured to receive the cartridge,
    wherein the cartridge body is configured to slide with respect to the enclosure from a first position in which the enclosure obstructs each of the first air inlet, the first air outlet, the second air inlet, and the second air outlet, to a second position in which the third air inlet is in fluid communication with the first air inlet, the third air outlet is in fluid communication with the first air outlet, the fourth air inlet is in fluid communication with the second air inlet, and the fourth air outlet is in fluid communication with the second air outlet, and wherein the cartridge assembly is configured so that insertion of the cartridge into the mouthpiece cavity moves the cartridge body from the first position to the second position.

2. The cartridge assembly according to claim 1,
wherein the cartridge body comprises a first cam surface protruding from the enclosure when the cartridge body is in the first position, and
wherein the first cam surface engages a first portion of the mouthpiece to move the cartridge body from the first position to the second position when the cartridge is inserted into the mouthpiece cavity.

3. The cartridge assembly according to claim 2, wherein at least one of the first cam surface and the first portion of the mouthpiece is tapered.

4. The cartridge assembly according to claim 3,
wherein the first cam surface is tapered,
wherein the mouthpiece defines an opening at an end of the mouthpiece cavity for receiving the cartridge, and
wherein at least part of the first portion of the mouthpiece defines part of an edge of the opening.

5. The cartridge assembly according to claim 1, wherein the cartridge assembly is further configured so that removal of the cartridge from the mouthpiece cavity moves the cartridge body from the second position to the first position.

6. The cartridge assembly according to claim 5,
wherein the cartridge body comprises a second cam surface protruding from the enclosure when the cartridge body is in the second position, and
wherein the second cam surface engages a second portion of the mouthpiece to move the cartridge body from the second position to the first position when the cartridge is removed from the mouthpiece cavity.

7. The cartridge assembly according to claim 6, wherein at least one of the second cam surface and the second portion of the mouthpiece is tapered.

8. The cartridge assembly according to claim 7, wherein the second portion of the mouthpiece comprises a tapered groove formed in an inner surface of the mouthpiece.

9. The cartridge assembly according to claim 6,
wherein the second cam surface is tapered,
wherein the mouthpiece comprises a slot, and
wherein at least part of the second portion of the mouthpiece defines part of an edge of the slot.

10. The cartridge assembly according to claim 1,
wherein the mouthpiece cavity is configured to slidably receive the cartridge along a first direction,
wherein the cartridge body is configured to slide with respect to the enclosure from the first position to the second position along a second direction, and
wherein the second direction is substantially orthogonal to the first direction.

11. The cartridge assembly according to claim 1, wherein the cartridge body is configured to slide with respect to the enclosure from the first position to the second position through a distance of less than 5 millimeters.

12. The cartridge assembly according to claim 1, wherein the cartridge body further comprises a nicotine source positioned within the first compartment and an acid source positioned within the second compartment.

13. The cartridge assembly according to claim 1,
wherein the cartridge body comprises a third compartment configured to receive a heating element of an aerosol-generating device, the third compartment positioned between the first compartment and the second compartment, and
wherein the enclosure comprises an aperture aligned with the third compartment when the cartridge body is in the second position.

14. The cartridge assembly according to claim 1, wherein the cartridge body comprises a susceptor positioned between the first compartment and the second compartment.

15. An aerosol-generating system, comprising:
a cartridge assembly according to claim 1; and
an aerosol-generating device comprising a device cavity configured to receive an upstream end of the cartridge assembly and a heater configured to heat the first compartment and the second compartment of the cartridge body of the cartridge assembly.

16. The aerosol-generating system according to claim 15,
wherein the heater comprises a heating element positioned within the device cavity,
wherein the cartridge body comprises a third compartment configured to receive the heating element and positioned between the first compartment and the second compartment, and
wherein the enclosure comprises an aperture aligned with the third compartment when the cartridge body is in the second position.

17. The aerosol-generating system according to claim 15,
wherein the heater comprises an inductive heater surrounding at least a portion of the device cavity, and
wherein the cartridge body comprises a susceptor positioned between the first compartment and the second compartment.

* * * * *